US 6,530,936 B1

(12) United States Patent
Yun (10) Patent No.: US 6,530,936 B1
(45) Date of Patent: Mar. 11, 2003

(54) APPARATUS FOR HARVESTING CARTILAGE

(76) Inventor: Yeong Seok Yun, 108-901 Daewoo 2-cha Apartment, Dongchoon-dong, Yeonsoo-ku, Incheon 406-130 (KR)

( * ) Notice: Subject to any disclaimer, the term of this patent is extended or adjusted under 35 U.S.C. 154(b) by 0 days.

(21) Appl. No.: 09/701,806

(22) PCT Filed: Jun. 3, 1999

(86) PCT No.: PCT/KR99/00274

§ 371 (c)(1),
(2), (4) Date: Dec. 1, 2000

(87) PCT Pub. No.: WO99/62396

PCT Pub. Date: Dec. 9, 1999

(30) Foreign Application Priority Data

Jun. 3, 1998 (KR) .............................. 98-20595

(51) Int. Cl.⁷ .............................................. A61B 17/32
(52) U.S. Cl. ......................... 606/167; 606/170; 606/79
(58) Field of Search ........................... 606/1, 155, 170, 606/171, 180, 112–114, 127, 128, 167, 96, 184, 185, 190, 191, 159, 79, 84; 600/562–565, 566, 567; 604/22, 164, 170, 17

(56) References Cited

U.S. PATENT DOCUMENTS

| | | | |
|---|---|---|---|
| 2,541,542 A | | 2/1951 | Perez et al. |
| 4,461,305 A | * | 7/1984 | Cibley |
| 5,133,360 A | | 7/1992 | Spears |
| 5,350,355 A | | 9/1994 | Sklar |
| 5,353,804 A | * | 10/1994 | Kornberg et al. |
| 5,522,827 A | * | 6/1996 | Combs et al. .............. 606/167 |
| 5,662,671 A | * | 9/1997 | Barbut et al. ................ 606/170 |
| 5,687,739 A | | 11/1997 | McPherson et al. |
| 5,817,034 A | * | 10/1998 | Milliman et al. ........... 600/566 |
| 6,077,231 A | * | 6/2000 | Milliman et al. ........... 600/567 |
| 6,383,145 B1 | * | 5/2002 | Worm et al. ................ 600/564 |

OTHER PUBLICATIONS

Rollin K. Daniel, "Rhinoplasty and Rib Grafts: Evolving a Flexible Operative Technique," Plastic and Reconstructive Surgery, Oct. 1994, pp. 597–609.

Seiichiro Kobayashi et al., "Endoscope–assisted rib cartilage harvesting," Ann Plast Surg 1995;35:571–575.

Kanetoshi Ohara et al., "Chest Wall Deformities and Thoracic Scoliosis after Coastal Cartilage Graft Harvesting," Plastic and Reconstructive Surgery, Apr. 1997, pp. 1030–1036.

Seiichiro Kobayashi et al., "Correction of Pectus Excavatum and Pectus Carinatum Assisted by the Endoscope," Plastic and Reconstructive Surgery, Apr. 1997, pp. 1037–1045.

* cited by examiner

Primary Examiner—Michael J. Milano
Assistant Examiner—Jessica R Baxter
(74) Attorney, Agent, or Firm—Timothy J. Keefer; Wildman, Harrold, Allen & Dixon (57) ABSTRACT

An apparatus for harvesting cartilage comprises a cartilage harvesting pipe(1) having a cutting blade(3), a drive unit for moving the cartilage harvesting pipe(1), a connecting member(21) for connecting the cartilage harvesting pipe(1) and the drive unit, and a cutting member(11) made of a wire to separate the cartilage from a cartilaginous tissue by cutting the cartilage which is harvested with the cartilage harvesting pipe(1). The apparatus harvests easily and safely cartilage as much as is necessary with minimal scaring of the chest wall or pain.

14 Claims, 7 Drawing Sheets

APPARATUS FOR HARVESTING CARTILAGE

CROSS REFERENCE TO RELATED APPLICATION

This application claims the priority of Korean patent application Ser. No. 1998-20595 filed on Jun. 3, 1998.

BACKGROUND OF THE INVENTION

1. Field of the Invention

The invention relates to an apparatus for harvesting cartilage, and more particularly to an apparatus for harvesting with ease and safety, a needed amount of cartilage from cartilaginous tissue of a human body.

2. Description of the Related Art

Surgeons have used alloplastic materials for augmentation rhinoplasty, thyroplasty. tympanoplasty, and correction of subglotuic and tracheal stenosis and wide nasal cavities caused by atrophic rhinitis.

However, these material can cause inflammation and hypersensitive reactions. Although there has been no official report of people developing cancer due to the material, some studies report that carcinogen has been found in the bodies of animals injected with the material.

To avoid the above noted side effects of the alloplastic material, many surgeons are performing the same operations using autogenous tissues found in bone, cartilage, dermis, fascia and the like. Of these, cartilage is used most abundantly by surgeons because it is easy to handle, there is little absorption after surgery and it is easily fixed to the receiving site.

However, in the septal and auricular cartilage, there is a limit to the amount of cartilage that can be harvested, and it takes a long time to remodel and suture these regions to suit the specific needs. Contrary to products made from the silicon, the shape of an end product made from septal or auricular cartilage is uneven at its margin as well as on its surface and is not perfectly straight.

Large amount of cartilage can be obtained from the coastal or rib cartilage. However, there is lingering pain and a relatively large scar left on the chest wall after harvesting rib cartilage with conventional surgery. Also, with known methods, unnecessarily large amounts of cartilage are extracted and deformity often occurs on the chest wall.

SUMMARY OF THE INVENTION

Accordingly, the object of the present invention is to provide an apparatus for harvesting cartilage easily and safely with minimal scaring of the chest wall or pain.

To accomplish the above object, the present invention provides an apparatus comprising a cartilage harvesting pipe having a cutting blade, a driving means for moving the cartilage harvesting pipe, a connecting member for connecting the cartilage harvesting pipe to the driving means, a cutting member made of a wire for separating the cartilage from a cartilaginous tissue by cutting the cartilage which is harvested using the cartilage harvesting pipe.

BRIEF DESCRIPTION OF THE DRAWINGS

Reference is made to the drawings for purposes of illustration only and not by way of limitation, and they illustrate the following.

DETAILED DESCRIPTION OF PREFERRED EMBODIMENTS

The present invention will now be described in further detail by way of example with reference to the accompanying drawings.

Figure 1:
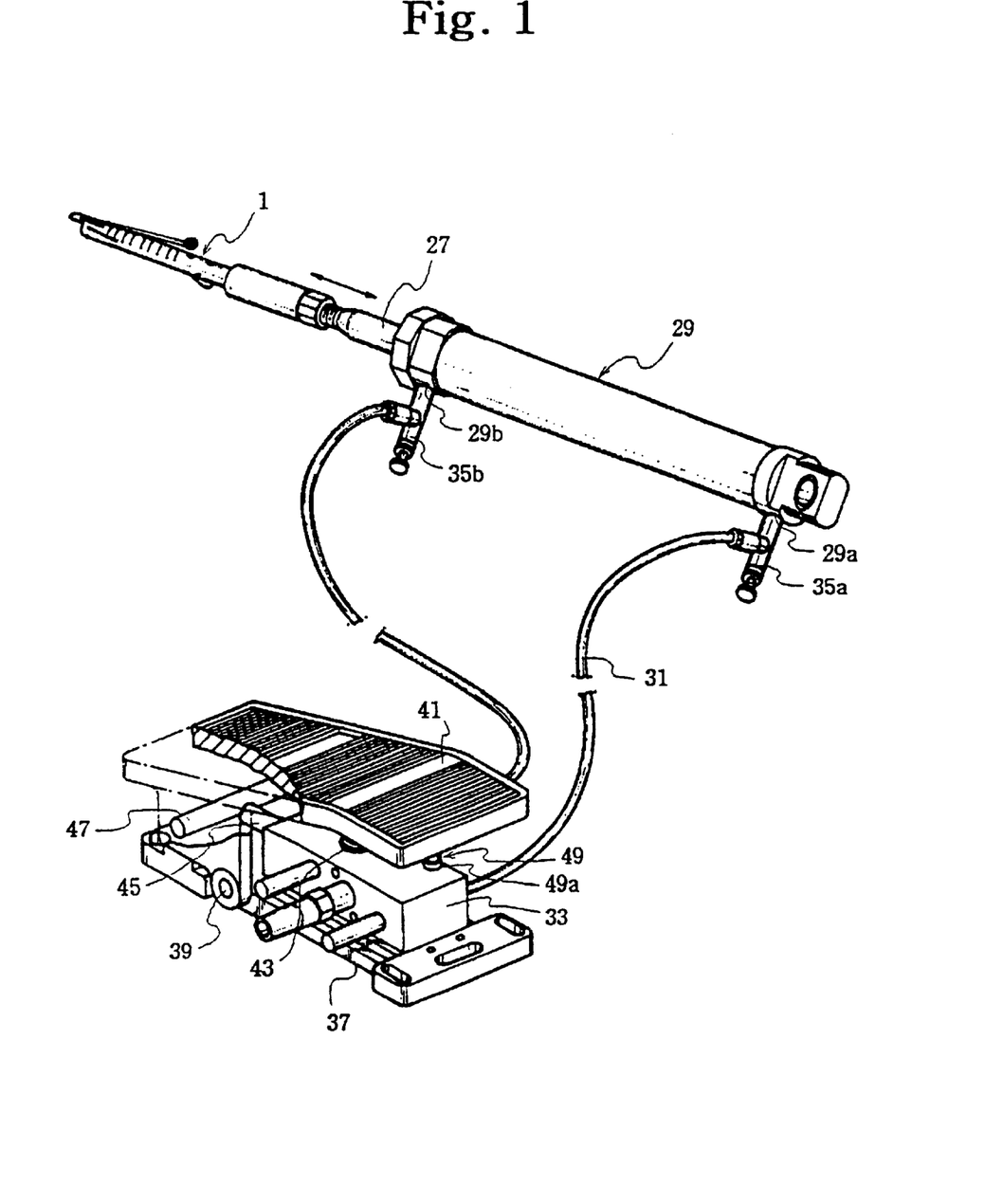
FIG. 1 is a perspective view depicting the apparatus for harvesting cartilage according to an embodiment of the invention.
Figure 4:
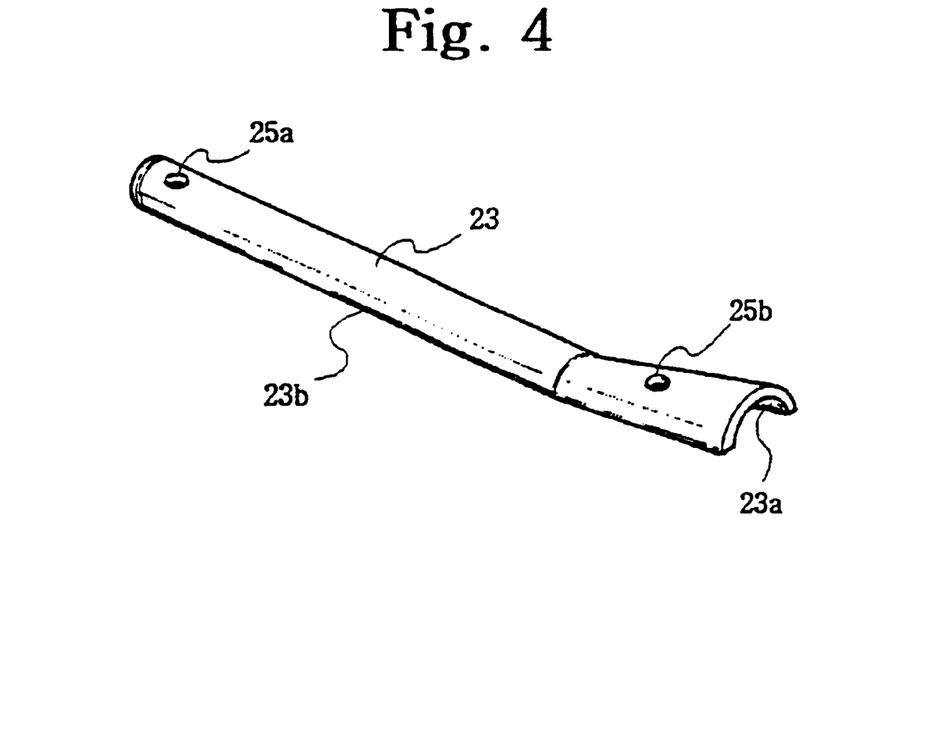
FIG. 4 is a perspective view depicting the guide member according to the present invention.

FIG. 1. shows an apparatus for harvesting cartilage according to an embodiment of the invention. The apparatus comprises a cartilage harvesting pipe (1) for harvesting cartilage, and a drive means which moves cartilage harvesting pipe (1) back and forth to ease harvesting with the aid of a guide member (23) (FIG. 4).

Figure 2:
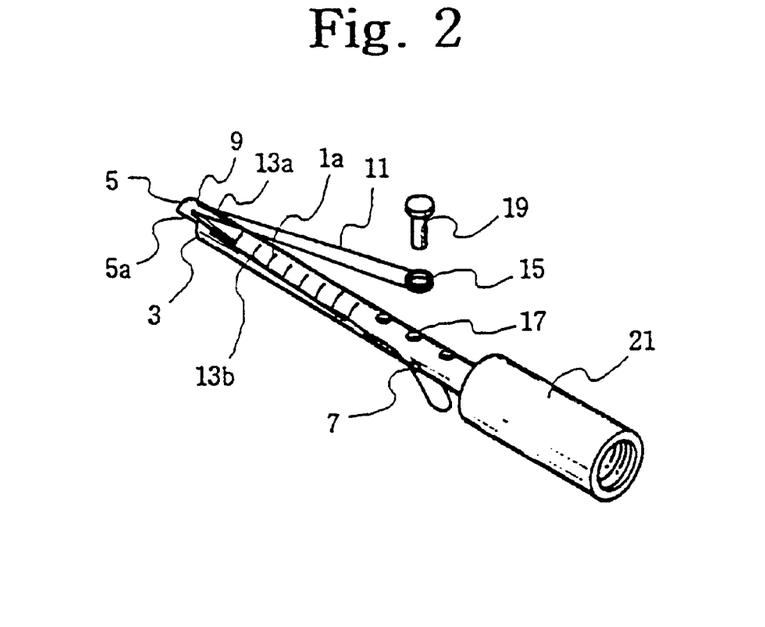
FIG. 2 is a perspective view depicting the cartilage harvesting pipe according to embodiment shown in FIG. 1.

FIG. 2 shows a cartilage harvesting pipe (1) according to the present invention. Cartilage harvesting pipe (1) has a cutting blade (3). Cutting blade (3) is formed on the edge of a front end of cartilage harvesting pipe (1). Also, cartilage harvesting pipe (1) has a guide plate (5). Guide plate (5) is formed in a portion of the front end of harvesting cartilage pipe (1) and the portion of the front end is projected more forward than the remained portion of the front end of cartilage harvesting pipe (1). Further, cartilage harvesting pipe (1) has a projection (7) which is formed on the lower part of the backward outer surface of the rear part of cartilage harvesting pipe (1).

Cartilage harvesting pipe (1) is preferably made of a steel having characteristics which resist wear and corrosion. Cartilage harvesting pipe (1) has a circular cross section. The diameter of cartilage harvesting pipe (1) may be adjusted depending on the purpose of the plastic surgery. For example, in order to avoid scaring the chest wall, the maximum allowable diameter of pipe (1) is determined after measuring the thickness of the target cartilage using ultrasonic technics.

Cartilage harvesting pipe (1) has notch marks (1a) which are positioned at predetermined intervals on the upper part of the outer surface to easily track the back and forth moving distance of pipe (1).

Figure 3A:
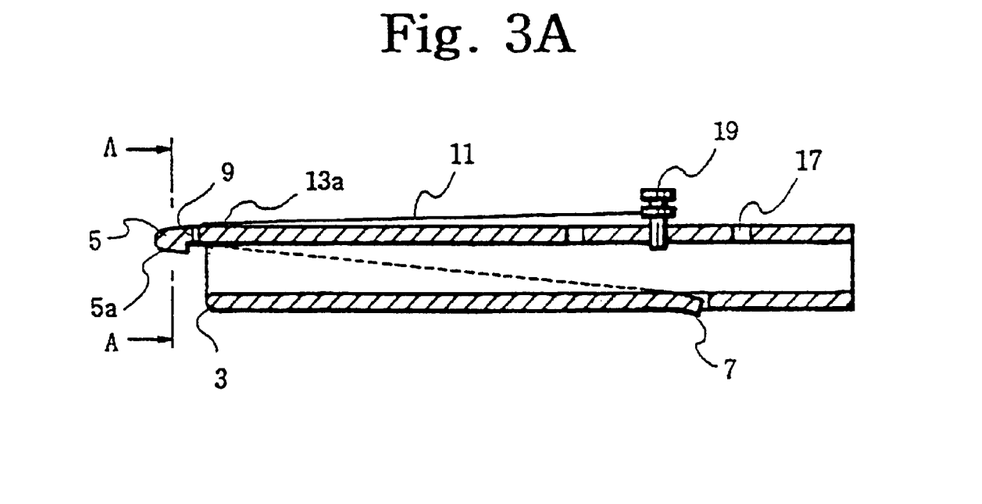
FIG. 3A is a cross-sectional view of the cartilage harvesting pipe of FIG. 2.
Figure 3B:
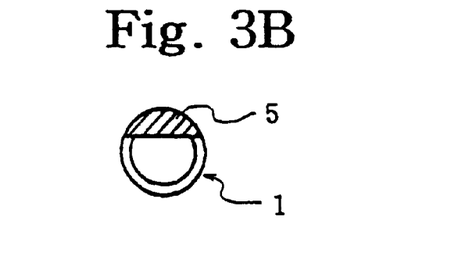
FIG. 3B is a cross-sectional view taken along line A—A in FIG. 3A.

Cutting blade (3) as shown in FIG. 3A, is made by grinding both inside and outside of the from end of pipe (1). If cutting blade (3) is made by grinding only the outside of the front end of pipe (1) cartilage harvesting pipe (1) does not progress easily, and cutting blade (3) often tends to deviate from the cartilaginous tissue.

Guide plate (5) of cartilage harvesting pipe (1) has a pair of through holes (9). The leading part of guide plate (5) is rounded off and a blade (5a) is formed along the rounded leading part thereby cartilage harvesting pipe (1) is inserted easily into the dermis and progress easily thereby.

The rear edge of the through hole (9) as shown in FIG. 3A, is also rounded off so that a cutting member (11) (FIG. 2) is easily moved back and forth in through hole (9).

Guide plate (5) serves as a safety device. Guide plate (5) prevents cartilage harvesting pipe (1) from invading coastal cartilage deeper than an operator expects and helps to harvest cartilage with consistent size. Guide plate (5) must be made thicker than the thickness of pipe (1). If guide plate (5) has the same thickness as pipe (1) it can penetrate the posterior part of the coastal cartilage and cause a pneumothorax.

FIG. 2. shows cutting member (11) for separating the cartilage from the cartilaginous tissue. Cutting member (11) passes through the pair of through holes (9). The middle portion of cutting member (11) is releasably hung on projection (7) and both ends of cutting member (11) are positioned on the upper part of the back of the outer surface of cartilage harvesting pipe (1).

Cutting member (11) is received on a pair of grooves (13a, 13b) which is formed in the vicinity of the front end of cartilage harvesting pipe (1), The width of the grooves (13a, 13b) is greater than the diameter of cutting member (11). This helps to minimize the contact area between cutting member (11) and the cartilaginous tissue and allows pipe (1) to move easily when pipe (1) harvests cartilage. Fix ring (15) is fixed at one of a plurality of holes (17) which are formed at a predetermined distance in the axial direction on.the upper part of the back of the outer surface of cartilage harvesting pipe (1) using a pin (19).

FIG. 3A shows cartilage harvesting pipe (1) to which a cutting member (11) is held. Referring in FIG. 3A. the middle part of cutting member (11) is hung on the projection (7) with passed through the hole of the guide plate (5), and fix rings (15) are connected to both ends of cutting member (11) and fixed on the upper part of cartilage harvesting pipe (1) by pin (19).

A connecting member (21), as shown in FIG. 2, is extended backward from the rear end of cartilage harvesting pipe (1). Connecting member (21) is detachably connected to piston rod (27). (FIG. 1). As cartilage harvesting pipe (1) can be separated it is convenient to sterilize it after an operation.

FIG. 4 shows a guide member (23) for inserting between the costal cartilage and the perichondrium and separating the two. Guide member (23) has a guide groove (23a, 23b) formed in the axial direction on the lower part thereof to guide the sliding of cartilage harvesting pipe (1) contacting guide plate (5) of cartilage harvesting pipe (1). It helps pipe (1) slide straight along the planned pathway on the coastal cartilage. A rear part of guide member (23) is inclined upwards to help pipe (1) slide inward. Also, guide member (23) has the first and second guide holes (25a, 25b) to fix guide member (23) to the coastal cartilage and the skin. The internal surfaces of guide holes (25a, 25b) are tapered for the pin and needle to be easily inserted.

Referring to again in FIG. 1. the drive means for moving cartilage harvesting pipe (1) will be explained.

The drive means, as shown in FIG. 1. comprises an air cylinder (29) which has a piston rod (27) detachably connected to connecting member (23) of cartilage harvesting pipe (1), a valve (33) for providing selective air pressure with first port (29a) and second port (29b) which are positioned on the piston head chamber and piston rod chamber in air cylinder (29) respectively and connecting to air cylinder (29) by hose (31), and velocity control valves (35a, 35b) which are positioned in first port (29a) and second port (29b) and controls the forward and backward moving velocity of cartilage harvesting pipe (1) by adjusting the air pressure of first port (29a) and second port (29b).

Valve (33) is operated by pedal type structure. Valve (33) is mounted on base (37). A pedal (41) is mounted rotatably to base (37) by a pivot pin (39). A spring (43) is mounted under pedal (41) the lower end of spring (43) is adapted to contact to the upper surface of valve (33). A drive rod (47) is mounted on the front of pedal (41) to operate an operating rod (45) of valve (33). Also, buffer member (49) is mounted on the lower surface of pedal (41) toward the back of spring (43), and helps to prevent pedal (41) from directly striking valve (33) during its rotation. A screw lug (49a) is mounted on the rear end of buffer member (49) to limit the rotation angle of pedal (41).

The procedure for harvesting cartilage will be explained with reference to FIGS. 5A to 5D.

Figure 5A:
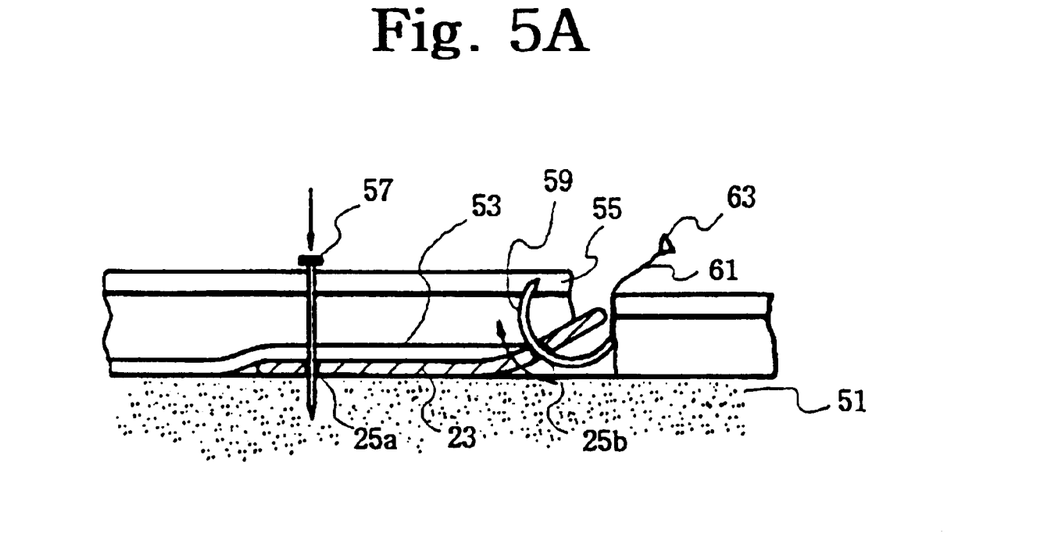
FIGS. 5A to 5D are schematic illustrations successively depicting the procedure for harvesting cartilage according to the present invention.

At first, a coastal cartilage for harvesting is selected. Fifth, sixth or seventh through ninth costal cartilage are the sites for harvesting. Using an ultra-sono on the coastal cartilages, the diameter and length of the cartilage and evidence of calcification are identified. Afterwards, an appropriate cartilage for harvesting is selected.

Minimal skin incision (approximately 1 to 1.5 cm) is made for input of the front end of cartilage harvesting pipe (1).

Using a perichondrial elevator, the perichondrium is elevated from the front surface of the coast cartilage.

As shown in FIG. 5A, guide member (23) is then inserted between the coastal cartilage (51) and perichondrium (53). Guide member (23) is fixed to coastal cartilage (51) using a straight needle (57) and to skin (55) using a curved needle (59). Curved needle (59) is attached to a string (61) and a small piece (63) is attached to the end of string (61).

Specifically, straight needle (57) is passed through first guide hole (25a) and thus fixes skin (55) to coastal cartilage (51). Curved needle (59) is passed through second guide hole (25b) under cut skin (55) and then comes out of skin (55).

After curved needle (59) comes out of skin (55), and as string (61) attached to curved needle (59) is pulled out, small piece (63) is halted in second guide hole (25b), thereby skin (55) is fixed to guide member (23) by string (61).

Figure 5B:
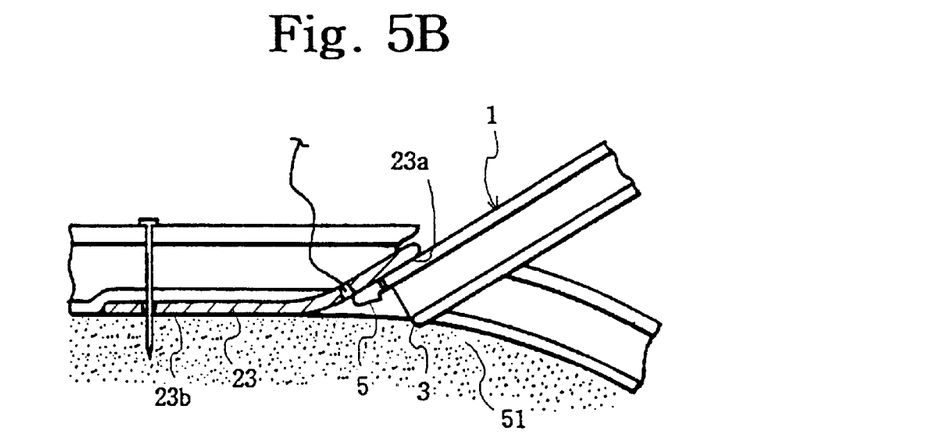

As shown in FIG. 5B, guide plate (5) of cartilage harvesting pipe (1) then slides beneath guide member (23). Cutting blade (3) is then progressed and cuts cartilage (51) until the predetermined amount of cartilage is obtained from coastal cartilage (51).

Figure 5C:
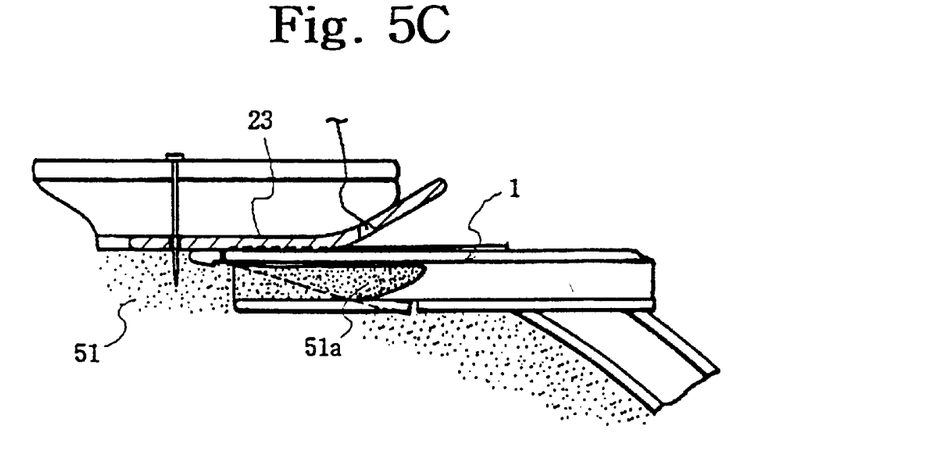

As shown if FIG. 5C, guide plate (5) is placed outside coastal cartilage (51) and simultaneously the middle and lower part of cartilage harvesting pipe (1) are placed inside coastal cartilage (51). Also, cartilage (51a) which is almost cut remains in cartilage harvesting pipe (1).

Figure 5D:
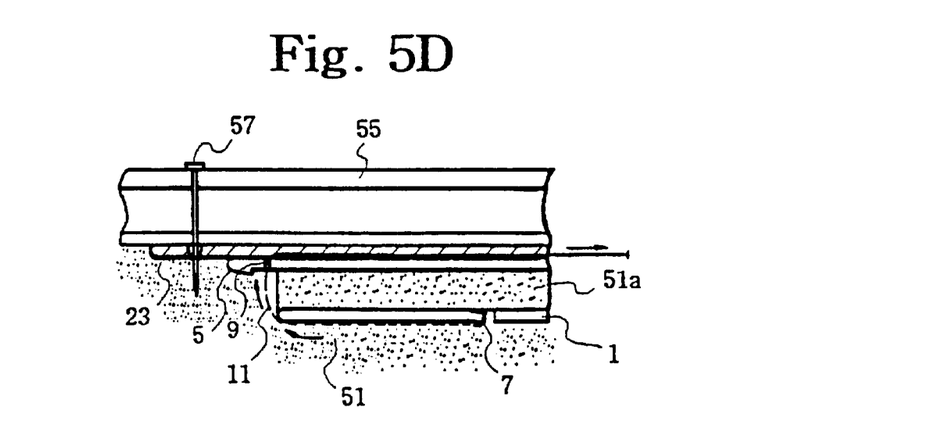

As pin (19) is pulled out of hole (17) of cartilage harvesting pipe (1), cutting member (11) hung on projection (7) comes loose and is released from projection (7) using a tool such as a pin (not shown). As fix ring (15) attached to cutting member (11) is pulled as shown in FIG. 5D, cutting member (11) slides forward along the outside of pipe (1) and then below guide plate (5), cartilage is totally snared and cut by cutting member (11).

Afterward, cartilage harvesting pipe (1) including cartilage is withdrawn, thereby the surgeon obtains the predetermined amount of the cartilage.

The backward and forward movement of cartilage harvesting pipe (1) will be explained.

When pedal (41) is depressed, pipe (1) moves forward. Specifically, as pedal (41) is depressed, drive rod (47) of pedal (41) pushes operating rod (45) and the air pressure reserved in the air tank (not shown) flows into first port (29a) of air cylinder (29) via open passage of valve (33) thereby piston rod (27) moves forward and simultaneously pipe (1) moves forward.

When pedal (41) is placed at the initial position, pipe (1) moves backward. Specifically as the force pushed on pedal (41) is removed, pedal (41) is placed back to initial position by the force of spring (43) and operating rod (45) of valve (33) is also placed back to the initial position. Valve (33) is then operated so that the air pressure may flow into second port (29b) of air cylinder (29), thereby piston rod (27) moves backward by the air pressure and simultaneously pipe (1) moves backward.

The moving velocity of cartilage harvesting pipe (1) is controlled by velocity control valves (35a, 35b) which adjust the amount of the air passing into and out of air cylinder (29). In this embodiment, nitrogen may also be used instead of air.

Figure 6:
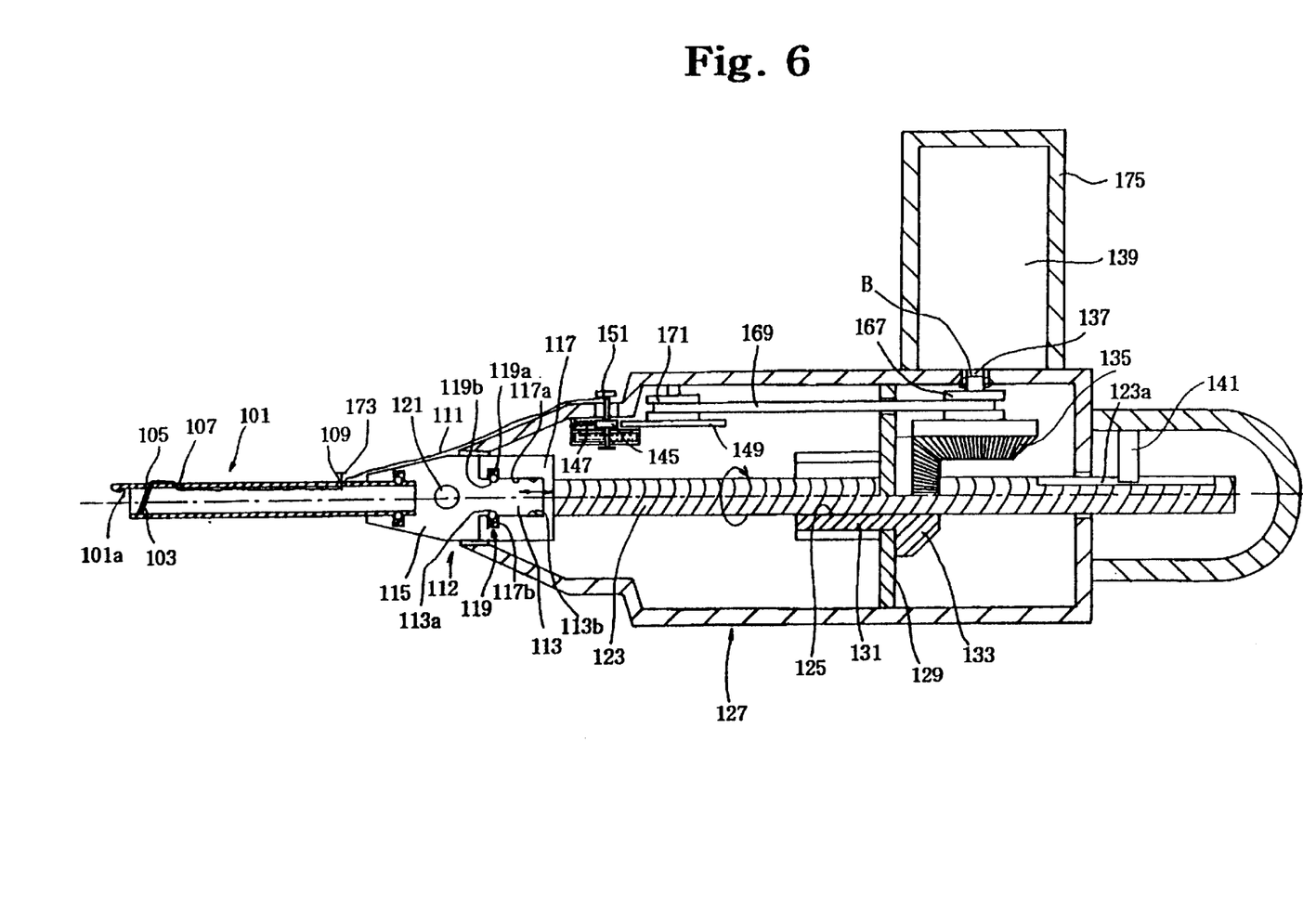
FIG. 6 is a cross sectional view depicting the interior construction of the apparatus for harvesting cartilage according to another embodiment of the invention.
Figure 7:
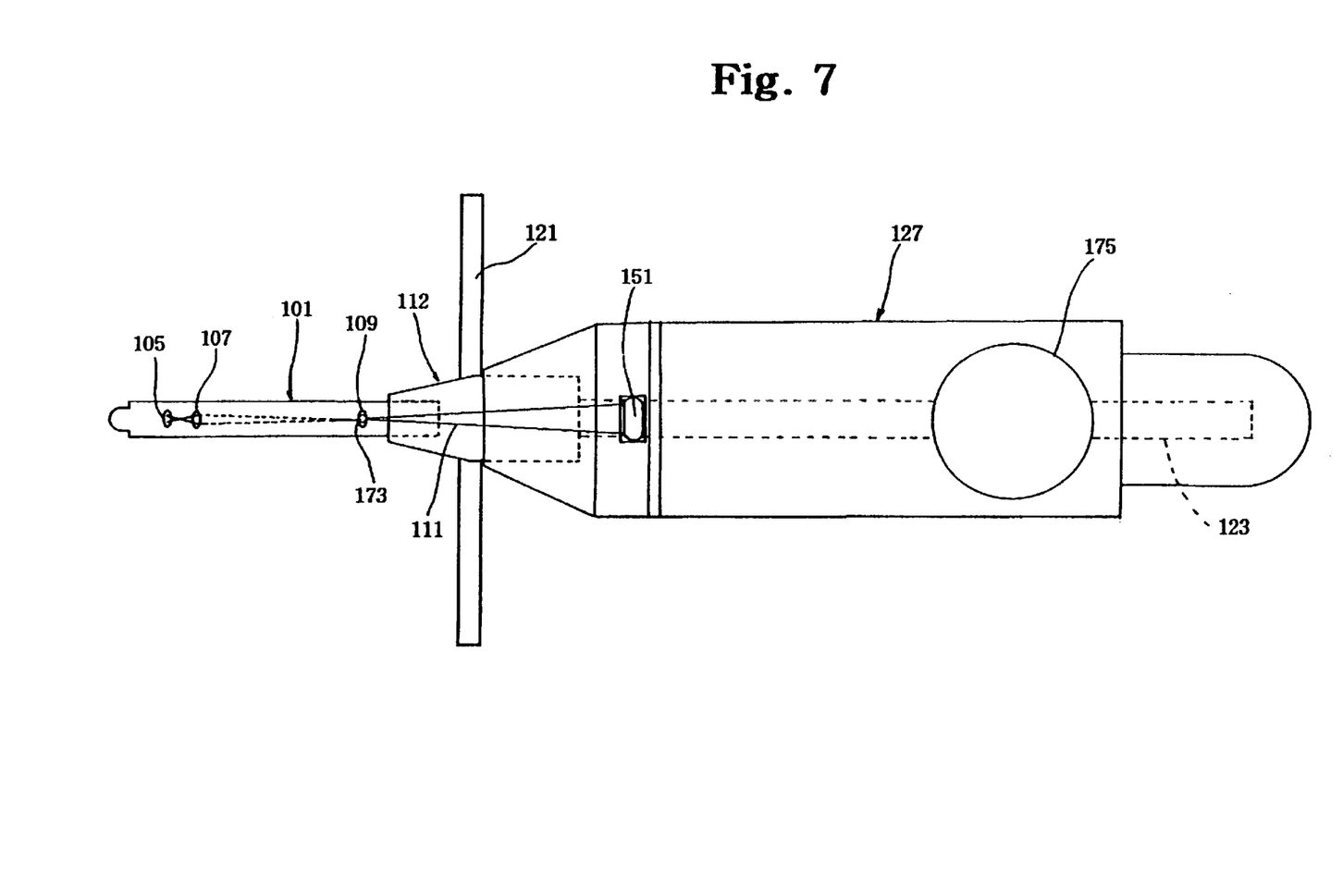
FIG. 7 is a top plan view of the apparatus shown in FIG. 6.

FIGS. 6 and 7 show another embodiment of the apparatus for harvesting cartilage.

Cartilage harvesting pipe (101) according to this embodiment, as shown, has a circular groove (103) which is formed to be inclined to the cross section of cartilage harvesting pipe (101) on the forward internal surface (101a) thereof. First hole (105) is formed on the upper portion of circular groove (103). Second hole (107) is formed backward in the vicinity of the first hole (105) and third hole (109) is formed in the vicinity of the rear end of cartilage harvesting pipe (101). These holes (105, 107, 109) are positioned in the axial direction on the upper part of cartilage harvesting pipe (101).

In this embodiment cutting member (111) is preferably made of a wire rope which has a diameter less than the depth of circular groove (103). Thus, cutting member (111) is not projected from the internal surface of pipe (101) on completely settling in circular groove (103). This helps to prevent cutting member (111) from interfering with the cartilage when pipe (101) cuts the cartilage.

Connecting member (112) includes first connecting member (115) which connects detachably to the rear portion of cartilage harvesting pipe (101) and has an extending part (113) extending backward and second connecting member (117) which has an inserting bore (117a) engaging extending part (113) of first connecting member (115).

At least one handle (121) is mounted on the both sides of first connecting member (115).

A plurality of stop members (119) are mounted on the forward internal surface of inserting bore (117a) so that second connecting member (117) may move back and forth within a range of a predetermined distance against first connecting member (115). Stop member (119) includes a spring (119a) mounted in groove (117b) which is formed on the internal surface of inserting bore (117a) and a ball (119b) which connects to an end of spring (119a). The upper portion of ball (119b) projects from the internal surface receiving the elastic force of spring (119a). Ball (119b) engages each of fix grooves (113a, 113b) which is formed on the outer surface of extending part (113) of second connecting member (117).

The drive means for this embodiment comprises a moving screw (123) which extends backwards from connecting member (112) of cartilage harvesting pipe (101), a screw member (131) which has a screw part (125) engaging moving screw (123) on the internal surface and is mounted rotatably to a vertical partition (129) which is formed vertically from a casing (127) enveloping moving screw (123) to the inside of casing (127), a driven bevel gear (133) which is mounted integrally to the one side of screw member (131) and envelopes moving screw (123), a drive bevel gear (135) for engaging driven bevel gear (133), a motor (139) having drive bevel gear (135) on the rotation shaft (137) thereof and transferring the rotation force into drive bevel gear (133), and a rotation preventing pin (141) which is projected downwards from the internal surface of casing (127) and engages a groove (123a) which is formed on the upper part of the back of the outer surface of moving screw (123).

One difference in this embodiment compared to the preferred embodiment is a means for promoting cutting of the cartilage by pulling alternately at each of the two ends of cutting member (111), back and forth.

Figure 8:
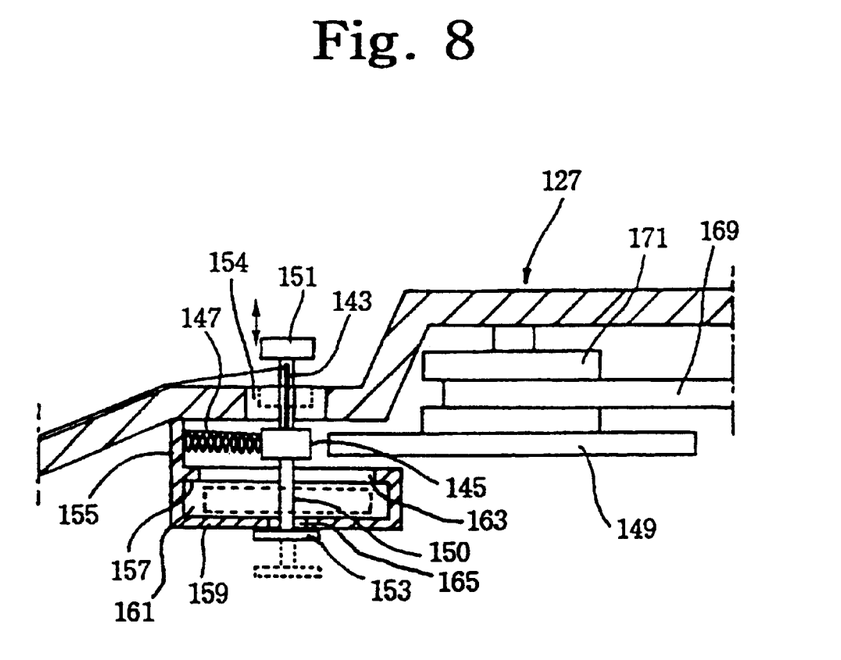
FIG. 8 is a fragmentary side view, on an enlarged scale, depicting means for promoting the cartilage cutting portion, shown in FIG. 6.
Figure 9:
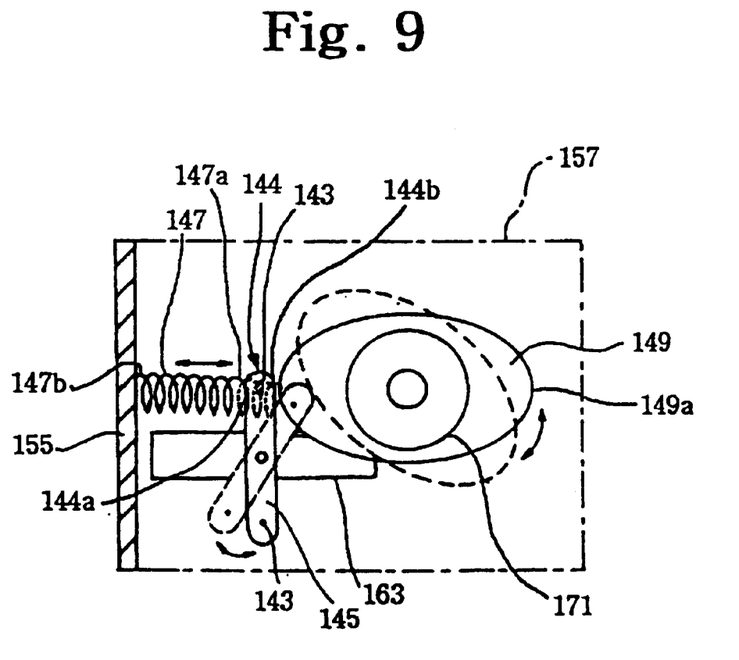
FIG. 9 is a schematic illustration depicting the operation of the rotating member for cutting cartilage, shown in FIG. 8.

The means for promoting cutting of the cartilage, as shown in FIGS. 8 and 9, includes rotating member (145) having a fix pin (143) which is connected to each of the two ends thereof and pivoted on the forward upper part of casing (127), a spring (147) having a free end (147a) directed to the front surface (144a) of one side (144) of rotating member (145) and a fix end (147b) fixed to the internal part of casing (127) and biasing backward one side (144) of rotating member (145), a cam (149) which has lobes (149a) pushing rear surface (144b) of one side (144) and rotating forward one side (144) of rotating member (145), and cam drive means for rotating cam (149).

Rotating member (145) is mounted to selectively receive the rotation force of cam (149). Referring to FIG. 8, a button (151) is mounted on the upper end of rotate shaft (150) of rotating member (145) in a direction longitudinal to the axis of rotating member (145) and a stopper (153) having a type of plate mounted on the lower end of rotation shaft (150). Opening (154) is formed on the forward upper part of casing (127) so that button (151) may move up and down through opening (154).

A support board (155) is formed downward from the upper internal surface of casing (127). and first board member (157) and second board member (159) which is spaced from first board member (157) are extended vertically to the side surface of support board (155). Space (161) formed between first board member (157) and second board member (159) has a size as much as rotating member (145) is sufficiently accommodated in it. Fix end (147b) of spring (147) is fixed to the upper part of the side surface of support board (155). Spring (147) is placed on first board member (157). First board member (157) has an opening (163) which has a size greater than that of rotating member (145) and has the same form as rotating member (145) and is formed, as shown, in the coaxial direction of casing (127). Second board member (159) has a hole (165) in which the shaft passes through. The area of hole (165) is smaller than that of stopper (153).

FIG. 9 shows rotating member (145) which is positioned to operate with cam (149). Button (151) is protruded over casing (127) and rotating member (145) contacts to cam (149). In this state, as button (151) is rotated to coincide with the axis of casing (127), rotating member (145) is then placed to drop into opening (163), and thus rotating member (145) is positioned in space (161) between first and second board member (157, 159) if button (151) is pushed to the position shown by the dotted line.

Therefore, rotating member (145) is placed to operate with cam (149) if button (151) is rotated toward opening (163) and pulled out until stopper (153) is stopped by second board member (159), whereas rotating member (145) is placed not to receive the rotation of cam (149) if button (151) is rotated toward opening (163) and pushed until rotating member (145) is positioned in space (161).

Referring to FIG. 6, a cam drive means includes a drive pulley (167) which is positioned in the vicinity of drive bevel gear (135) on the rotation axis of motor (139), and a driven pulley (171) which is mounted rotatably on the internal surface of casing (127) in the position spaced from drive pulley (167) to forward casing (127) and attached to the side surface of cam (149) and connected to drive pulley (167) via a belt (169) to receive the rotation force of motor (139).

The procedure of the operation using this apparatus will be explained.

At first, cutting member (111) is assembled on cartilage harvesting pipe (101). Referring to FIG. 7, the middle portion of cutting member (111) passes through first hole (105) and then is inserted into circular groove (103) and maintained in circular form in groove (103). Both ends of cutting member (111) are then inserted into second hole (107) and passes through the internal space of cartilage harvesting pipe (101) and comes out of third hole (109). The rear part of the cutting member (111) comes out of third hole (109) and pin (173) is temporarily fixed to third hole (109).

Each of the two ends of cutting member (111) is then fixed to fix pin (143) of rotating member (145).

After cutting member (111) is assembled onto cartilage harvesting pipe (101), the surgeon manipulates button (151) so that rotating member (145) does not operate with cam (149). Next, the surgeon moves cartilage harvesting pipe (101) forward to harvest cartilage.

The operation for moving forward cartilage harvesting pipe (101) will be explained.

The operator grips handle (121) and a part (175) of casing (127) which encloses motor (139), respectively, and turns on motor (139). The rotation force of motor (139) is transferred to drive bevel gear (135), driven bevel gear (133), and moving screw (123). Moving screw (123) receives the rotation force of driven bevel gear (133) via screw member (131), but moving screw (123) can not rotate since the rear part of moving screw (123) is fixed by rotation preventing pin (141), thereby moving screw (123) only moves in a straight direction. The moving direction of moving screw (123) is dependent on the rotating direction of motor (139).

For example, as shown in FIG. 6, if the rotate shaft of motor (139) is rotated in a counterclockwise direction B, moving screw (123) moves forward. During the forward movement of cartilage harvesting pipe (101), rotating member (145) is placed so that it does not operate with cam (149).

The procedure for harvesting a cartilage by moving forward cartilage harvesting pipe (101) is here abbreviated since the procedure was previously described in detail in conjunction with FIGS. 5A to 5C.

The manner of the work for separating the cartilage in pipe (101) from the cartilaginous tissue will be explained.

Cartilage harvesting pipe (101) is temporarily stopped beneath guide member (112), as button (151) is placed to pass opening (163) and then pulled out. Rotating member (145) is then placed to operate with cam (149). Under such a state, the surgeon holds handle (121) so that it does not deviate cartilage harvesting pipe (101) from that position and then operates motor (139) so that cartilage harvesting pipe (101) may move backward. Next, second connecting member (117) moves backward together with moving screw (123) against first connecting member (115) held in the predetermined position until ball (19b) halted in groove (113a) is inserted into groove (113b).

Simultaneously, drive pulley (167) mounted on the shaft of motor (139) transfers the rotation force to driven pulley (171) via belt (169), thereby cam (149) integral to driven pulley (171) is rotated to operate rotating member (145).

FIG. 9 shows the manner of operation for rotating member (145) according to the rotation of cam (149).

As shown, each of the two ends of rotating member (145) alternately moves back and forth in the range of a predetermined rotation angle by rotation of cam an (149), thereby, rotating member (145) performs a see-saw motion. This see-saw motion of rotating member (145) results in a movement pulling alternately each of the two ends of cutuing member (111) back and forth. Thus, the middle part of cutting member (111) in circular groove (103) undergoes a movement along circular groove (103) enclosing the cartilage upon changing the movement direction in turn, but dose not help to cut the cartilage since cutting member (111) is not yet contacted with the cartilage at that time.

The motion for totally cutting the cartilage occurs when the surgeon pulls casing (127) against handle (121) during the operation of rotating member (145). Specifically, as casing (127) is pulled with handle (121) being held in a predetermined position, rotating member (145) mounted on casing (127) is also moved backward, thereby cutting member (111) contacts to the cartilage released from circular groove (103).

At this time, the back and forth movement of cutting member (111) promotes cutting of the cartilage.

After the cartilage is separated, the middle part of cutting member (111) comes out of first hole (105) and enters second hole (107) by pulling cutting member (111), and is finally placed in cartilage harvesting pipe (101).

The foregoing invention has been described in terms of exemplary embodiments. However, those skilled, in the art will recognize that many variations to such embodiments are possible. Such variations are intended to be within the scope of the present invention and the appended claims.

What is claimed is:

1. An apparatus for harvesting cartilage, comprising:
    a cartilage harvesting pipe having a cutting blade formed on the edge of a front end of the cartilage harvesting pipe and a guide plate formed in a portion of the front end of the harvesting cartilage pipe, the portion of the front end projecting more forward than the remaining portion of the front end of the cartilage harvesting pipe;
    a driving means for moving the cartilage harvesting pipe;
    a connecting member for connecting the cartilage harvesting pipe to the driving means; and
    a cutting member made of a wire for separating the cartilage from a cartilaginous tissue by cutting the cartilage which is harvested using the cartilage harvesting pipe,
    wherein the guide plate has through holes and a projection which is formed on the lower part of the back outer surface of the rear part of the cartilage harvesting pipe, the cutting member passes through the through holes, the middle portion of the cutting member releasably hung on the projection, and the two ends of the cutting member being positioned on the upper part of the back outer surface of the cartilage harvesting pipe.

2. The apparatus of claim 1, wherein the cartilage harvesting pipe has a pair of grooves which are formed in the vicinity of the front end thereof, for receiving the cutting member.

3. The apparatus of claim 1, wherein the apparatus further comprises fix rings which are connected with the two ends of the cutting member, a plurality of holes being formed at a predetermined distance in the axial direction on the upper part of the back outer surface of the cartilage harvesting pipe, and the fix ring being fixed at one of the plurality of holes using a pin.

4. The apparatus of claim 1, wherein the cartilage harvesting pipe has a circular groove which is formed to be inclined to the cross section of the cartilage harvesting pipe on the forward internal surface thereof, a first hole being formed on the upper portion of the circular groove, a second hole formed backwards in the vicinity of the first hole and a third hole formed in the vicinity of the rear end of the cartilage harvesting pipe being positioned in the axial direction on the upper part of the cartilage harvesting pipe, the middle portion of the cutting member passing through the first hole, inserted into the circular groove and maintained in circular form in the groove, the two ends of the cutting member inserted into the second hole, passed through the internal space of the cartilage harvesting pipe, exiting the third hole, and positioned on the upper part of the backward outer surface of the cartilage harvesting pipe.

5. The apparatus of claim 4, wherein the cutting member is made of a wire rope which has a diameter less than the depth of the circular groove.

6. The apparatus of claim 4, wherein the connecting member includes a first connecting member which connects detachably to the rear portion of the cartilage harvesting pipe and has a extending part extending backward, and a second connecting member which has an inserting bore engaging the extending part of the first connecting member, a plurality of stop members being mounted on the forward internal surface of the inserting bore so that the first connecting member may not separate from the second connecting member.

7. The apparatus of claim 4, wherein at least one handle is mounted on the both sides of the first connecting member.

8. The apparatus of claim 1, wherein the apparatus further comprises a guide member which is inserted between the cartilage and perichondrium and has a guide groove forming in the axial direction on the lower part thereof to guide the sliding of the cartilage harvesting pipe contacting the guide plate of the cartilage harvesting pipe.

9. The apparatus of claim 8, wherein a rear part of the guide member is inclined upwards with the rear part having at least one hole.

10. The apparatus of claim 1, wherein the driving means comprises an air cylinder which has a piston rod connected detachably to the connecting member of the cartilage harvesting pipe and has a piston rod chamber and a piston head chamber therein, a valve for providing selective air pressure to a first port and a second port which are positioned on the piston head chamber and the piston rod chamber in the air cylinder, respectively, and velocity control valves which are positioned in the first port and the second port and controls the forward and backward moving velocity of the cartilage harvesting pipe by adjusting the air pressure of the first port and the second port.

11. The apparatus of claim 1, wherein the driving means comprises a moving screw which extends backwards from the connecting member, a screw member which has a screw part engaging the moving screw on the internal surface and is mounted rotatably to a vertical partition which is formed vertically from a casing enveloping the moving screw to the inside of the casing, a driven bevel gear which is mounted integrally to one side of the screw member and envelopes the moving screw, a drive bevel gear for engaging the driven bevel gear, a motor having the drive bevel gear on the rotation shaft thereof which transfers the rotation force into the driven bevel gear, and a rotation preventing pin which is projected downward from the internal surface of the casing and engages a groove which is formed on the upper part of the back outer surface of the moving screw.

12. The apparatus of claim 11, wherein the apparatus further comprises means for promoting cutting of the cartilage by pulling alternately each of the two ends of the cutting member back and forth.

13. The apparatus of claim 12, wherein the means for promoting cutting of the cartilage includes a rotating member having a fix pin which is connected to each of the two ends thereof and pivoted on the forward upper part of the casing, a spring having a free end directed to the front surface of one side part of the rotating member and a fix end fixed to the internal part of the casing and biasing backward one side of the rotation member, a cam which has lobes pushing the rear surface of the one side and rotating forwards the one side of the rotation member, and cam drive means for rotating the cam.

14. The apparatus of claim 13, wherein the cam drive means includes a drive pulley which is positioned in the vicinity of the drive bevel gear on the rotation shaft of the motor, and a driven pulley which is mounted rotatably on the internal surface of the casing at a position spaced from the drive pulley to the forward casing and attached to the side surface of the cam and connected to the drive pulley via a belt to receive the rotation force of the motor.

* * * * *